United States Patent [19]

Larkin

[11] 4,395,578

[45] Jul. 26, 1983

[54] OLIGOMERIZATION OF OLEFINS OVER BORON TRIFLUORIDE IN THE PRESENCE OF A TRANSITION METAL CATION-CONTAINING PROMOTER

[75] Inventor: John M. Larkin, Austin, Tex.

[73] Assignee: Texaco, Inc., White Plains, N.Y.

[21] Appl. No.: 389,738

[22] Filed: Jun. 18, 1982

[51] Int. Cl.$^3$ .......................... C07C 1/16; C07C 2/02
[52] U.S. Cl. ........................................ 585/10; 585/12; 585/18; 585/255; 585/520; 585/525
[58] Field of Search ...................... 585/10, 12, 18, 255, 585/510, 512, 520, 522, 525, 526, 532, 643, 648, 660

[56] References Cited

U.S. PATENT DOCUMENTS 4,172,855  10/1979  Shubkin et al. ...................... 585/255
4,214,112   7/1980  Mandai et al. ...................... 585/532
4,225,739   9/1980  Nipe et al. .......................... 585/525

Primary Examiner—Curtis R. Davis
Attorney, Agent, or Firm—Jack H Park; Kenneth R. Priem; David L. Mossman

[57] ABSTRACT

Alpha olefins may be oligomerized over a boron trifluoride catalyst and a promoter containing a transition metal cation. When the oligomers are hydrogenated they provide a synthetic lubricant base stock having excellent properties. The alpha olefins may be derived from ethylene polymerization or wax pyrolysis. A protonic promoter and an inert organic solvent may be present.

47 Claims, No Drawings

OLIGOMERIZATION OF OLEFINS OVER BORON TRIFLUORIDE IN THE PRESENCE OF A TRANSITION METAL CATION-CONTAINING PROMOTER

BACKGROUND OF THE INVENTION

1. Field of the Invention

The invention relates to methods of oligomerizing olefins over a boron trifluoride catalyst together with a promoter, and more particularly relates to methods of oligomerizing a mixture of alpha olefins over a boron trifluoride catalyst in the presence of a promoter containing a transition metal cation.

2. Description of Related Methods

Nearly all of the patents issued on olefin oligomerization have involved alpha olefins. For example, see U.S. Pat. No. 3,410,925 to Eby, et al. in which alpha olefins are mixed with alkylatable aromatic hydrocarbons over a Friedel-Crafts catalyst to form an alkylation sludge which is then mixed with olefins having 3 to 18 carbon atoms which are also passed over the catalyst to produce olefin dimers. U.S. Pat. No. 3,652,706 to Saines, et al. describes the polymerization of alpha olefins having 2 to 20 carbon atoms over a Friedel-Crafts metal halide catalyst plus a hydrogen form of mordenite to produce compounds having a molecular weight between 700 and 2,500. Production of a gasoline fuel composition is described in U.S. Pat. No. 3,749,560 to Perilstein which occurs by reacting a mixture of mono olefins over a Friedel-Crafts catalyst heated to a temperature around 145° C. to produce oligomers having molecular weights between 350 to 1,500. Also, U.S. Pat. No. 3,149,178 to Hamilton, et al. reveals an improved method for making polymerized olefin synthetic lubricants via a particular distillation technique of oligomers made from alpha mono olefins using a Friedel-Crafts catalyst. Alpha olefins having six to twelve carbon atoms may be dimerized in the presence of a Friedel-Crafts catalyst according to the method described in U.S. Pat. No. 4,172,855 to Shubkin, et al.

It is also known that the term "Friedel-Crafts catalysts" includes boron trifluoride among other metal halide-type Lewis catalysts, see *Kirk-Othmer Encyclopedia of Chemical Technology*, Third Edition, Vol. 11, pg 292. Boron trifluoride has also been known to polymerize olefins, as seen in F. Albert Cotton, et al., *Advanced Inorganic Chemistry: A Comprehensive Text*, Interscience Publishers, 1962, p. 191.

A number of patents have also used $BF_3$ to oligomerize olefins. For example, British Pat. No. 1,323,353 describes the use of wax cracked alpha olefins as precursors for synlube fluids. U.S. Pat. No. 2,780,664 to Serniuk describes the reaction of conjugated dienes with mono olefins over $BF_3$ promoted by an ether mixed with a halo alkane diluent at a temperature from $-30$ to $100°$ C. to produce oligomers suitable for drying oils. Alpha olefins having from 5 to 20 carbon atoms are oligomerized using $BF_3$ plus an alcohol or water promoter as described in U.S. Pat. No. 3,382,291 to Brennan. In this patent, $BF_3$ and a mixture of $BF_3$ plus the promotor complex are introduced in two separate streams. Another U.S. Pat. No. by Brennan, 3,742,082, concerns the dimerization of alpha olefins via $BF_3$ which is promoted with phosphoric acid or water at a temperature from 100 to 150° C. U.S. Pat. No. 3,763,244 to Shubkin, which describes the oligomerization of n-alpha olefins having 6 to 16 carbon atoms over $BF_3$ promoted with water, at a temperature between 10 and 60° C. where it is preferred that $BF_3$ is added continuously.

Yet another U.S. Pat. No. to Brennan 3,769,363 describes the oligomerization of olefins having 6 to 12 carbon atoms using $BF_3$ with a carboxylic acid promoter having at least 3 carbon atoms at a temperature between 0 and 20° C. to produce olefins heavy in trimer form. U. S. Pat. No. 3,780,128 also to Shubkin relates to the oligomerization of alpha olefins having 6 to 16 carbon atoms in which $BF_3$ is employed in a molar excess of alcohol. U.S. Pat. No. 3,876,720 to Heilman, et al. describes a two-step procedure by which alpha olefins having 8 to 12 carbon atoms are converted to vinylidene olefins which are then reacted over a 1:1 molar complex of $BF_3$ and alcohol to produce oligomerized vinylidene olefins. A method for oligomerizing both short and long chain alpha olefins having from 14 to 20 carbon atoms simultaneously over $BF_3$ with an alcohol or water promoter at 0 to 60° C. with a monomer recycle is described in U.S. Pat. No. 4,225,739 to Nipe, et al. There is also U.S. Pat. No. 4,263,465 to Sheng, et al. which describes a two-step process for reacting 1-butene with a higher alpha olefin over $BF_3$ in the presence of a proton donor at a temperature from $-30$ to 50° C. to produce an oligomer having 8 to 18 carbon atoms. The intermediate oligomer is reacted with other higher alpha mono olefins over the same catalyst system from $-30$ to 60° C. to produce oligomers having 20 to 40 carbon atoms. For more information on $BF_3$-catalyzed oligomerization of alpha olefins, see Brennan, "Wide-Temperature Range Synthetic Hydrocarbon Fluids," Ind. Eng. Chem. Prod. Res. Dev. 1980, Vol. 19, pp 2–6 and Shubkin, et al., "Olefin Oligomer Synthetic Lubricants: Structure and Mechanism of Formation," Ind. Eng. Chem. Prod. Res. Dev. 1980, Vol. 19, pp 15–19.

U.S. Pat. No. 4,213,001 reveals a method of homopolymerizing an alpha olefin by utilizing boron trifluoride under pressure in the presence of a suspended particulate absorbent material. The absorbent material may be silica, alumina, magnesia, zirconia, activated carbon, the zeolites, silicon carbon, silicon nitride, titania, thoria, porous polyvinyl alcohol beads, porous polyethylene glycol beads and the like.

U.S. Pat. No. 4,300,006 issued on Nov. 10, 1981. It describes a process for producing a hydrocarbon oil by contacting a mixture of alpha and at least 50 weight percent internal olefins with a boron trifluoride dimerization catalyst. However, the productivity of useful products from the process revealed in U.S. Pat. No. 4,300,006 is quite low. For example, an alkane diluent is found to be necessary in the process described therein. When the lights and heavies are distilled out as required by the method, little useful product results. Further, this method requires a much longer reaction time and a higher catalyst concentration than desired. It would be beneficial if a method for producing synthetic lubricants could be devised which would overcome the aforementioned disadvantages.

Of particular interest is U.S. Pat. No. 4,214,112. It discloses a process for producing an olefin oligomer which involves polymerizing olefins having not less than 6 carbon atoms in the presence of a specified catalyst system. The system consists of an aluminum halide, a polyhydric alcohol derivative and a nickel compound or a cobalt compound. The nickel and cobalt compounds are listed as nickel carbonate, nickel tetracarbonyl, nickel nitrate, nickel monoxide, trinickel tetroxide, nickel sequioxide, nickel hydroxide, nickel sulfide, nickel sulfate, nickel acetate, nickel oleate, nickel stearate, nickel diatomaceous earth, nickel chloride, nickel acetylacetonate, nickel peroxide, cobalt carbonate, dicobalt octacarbonyl, cobalt chloride, cobalt nitrate, cobalt oxide, cobalt hydroxide, cobalt sulfide, cobalt sulfate, cobalt acetate, cobalt oleate, cobalt acetylacetonate, etc. and combinations thereof. The compounds used in the examples therein are nickel oxide, nickel chloride, nickel oleate, nickel carbonate and cobalt chloride.

In the field of oligomerizing olefins for synthetic lubricants, it is a continual problem to produce olefins having low viscosities at room temperature and below but which have a high viscosity index and low volatility.

SUMMARY OF THE INVENTION

The invention is concerned with a process for the oligomerization of mono olefins comprising contacting a mixture of alpha mono olefins having between 3 and 18 carbon atoms inclusive, with a catalyst comprising boron trifluoride in the presence of an organic promoter containing a transitional metal cation, under oligomerization conditions.

DESCRIPTION OF THE PREFERRED EMBODIMENTS

It has been surprisingly discovered that oligomers which have an unusual blend of properties may be made by reacting alpha mono olefins over a boron trifluoride catalyst and a promoter containing a transition metal cation. No other researchers have accomplished this objective in this way.

The olefin feedstock may be generally expressed as a mixture of alpha olefins having the formula

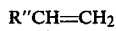

where R" is an alkyl radical of 1 to 16 carbon atoms. The total number of carbon atoms in the alpha olefins should range from 3 to 18. It is especially preferred that two sizes of olefins be used; namely, at least one alpha olefin having 3 to 5 carbon atoms (propylene, 1-butene and 1-pentene) and at least one higher molecular weight alpha olefin having 8 to 18 carbon atoms. This combination of low and high molecular weight olefins helps contribute to the unique properties of the resulting oligomers.

The higher alpha olefins to be oligomerized in this invention may be obtained by a multi-step process. In the first step, ethylene is transformed into linear alpha olefins using Ziegler technology as disclosed in various patents, including U.S. Pat. Nos. 3,424,815; 3,482,000; 3,424,816; 3,444,264; 3,444,263; 3,502,741; 3,510,539; 3,478,124; and 3,441,631. These patents are incorporated herein by reference. The result of this conversion of ethylene is a mixture of alpha olefins ranging from C-4 to above C-24. The alpha olefins ranging from about C-4 or C-8 to C-18 or any other range of alpha olefins desired within C-4 to C-24 are separated and oligomerized using boron trifluoride and the promoter of this invention. The alpha olefins of below about 8 and above about 18 carbon atoms are combined and subjected to an isomerization/disproportionation process described in the literature, for example: U.S. Pat. Nos. 3,647,906; 3,728,414 and 3,726,938, which are incorporated herein by reference.

The olefins resulting from this isomerization/disproportionation process are a mixture of alpha and internal olefins of various molecular weights. The olefins should have a total number of carbon atoms in the range from about 8 to 18 or any selected cut within that range may be oligomerized with boron trifluoride and a protonic promoter. Those olefins may be mixed with the alpha olefins from the initial ethylene made feed and oligomerized.

Such a process provides a systematic way to control which olefin cut is selected for oligomerization, and also uses the discarded cuts for additional feed. Olefins useful in the method of this invention may also be produced by wax pyrolysis.

Generally, the weight ratio of the low molecular weight alpha olefins ($C_3$–$C_5$) to the higher molecular weight alpha olefins is preferred to range from 0.5:1 to 3:1.

The catalyst of choice is boron trifluoride. However, it is well known that boron trifluoride by itself is not very effective and promoters (sometimes called co-catalysts) must be employed to activate the boron trifluoride. It has been surprisingly discovered that inorganic promoters which contain a transition metal cation are especially effective as promoters for $BF_3$. It is preferred that the transition metal be selected from the group consisting of nickel, copper, cobalt and chromium. It is especially preferred that the inorganic promoter be selected from the group consisting of elemental nickel, elemental copper, nickel oxide, copper oxide, chromium oxide, nickel fluoride, cobaltous carbonate, cobaltous fluoride and cobalt tetrafluoroborate, and mixtures thereof. Typical of useful mixtures of promoters are the nickel-copper-chromium oxides and cobalt-copper-chromium oxide combinations. These mixtures are known as hydrogenation-dehydrogenation catalysts and may be made by the procedure outlined in U.S. Pat. No. 3,152,998, incorporated by reference herein.

It is preferred that the boron trifluoride catalyst be present in an amount of from 0.2 to 3.0 weight percent, based on the olefin mixture amount. On the other hand, the transition metal promoter should be present in an amount of from about 0.005 to 3.0 weight percent, based on the olefin mixture amount.

Optionally, a number of different kinds of protonic promoters may be used, such as alcohols, carboxylic acids or water. It is especially preferred that 1-butanol be used as the promoter. Likewise, one skilled in the art may find an inert, organic solvent, such as cyclohexane, useful in conducting the oligomerization. However, the amount of solvent should be less than about 30 weight percent based on the olefin mixture. The temperature range at which the oligomerization may be performed successfully is between 25 and 125° C., with a preferred range between 30 to 120° C. The pressure range of the reaction may run from zero to 1,000 psig although autogenous pressures are preferred. The oligomerization of the olefins may be conducted in a batch or continous mode.

In order to form materials which have adequate oxidative stability for lubricants, the oligomerized olefins are optionally hydrogenated either partially or totally. This hydrogenation is done by procedures known to those skilled in the art as exemplified by U.S. Pat. Nos. 4,045,508; U.S. 4,013,736; U.S. 3,997,622 and U.S. 3,997,621. A particularly preferred catalyst for this hydrogenation is a nickel-copper-chromium oxide catalyst described in U.S. 3,152,998, discussed earlier. A cobalt-copper-chromium oxide catalyst would also be useful.

Kinematic viscosities at the standard temperature of 210° F. are given in centistokes. The viscosity index (VI) is the change in viscosity with temperature such that the higher the number, the lower is the change in viscosity with temperature. Conversely, a low VI signifies a large change in viscosity with temperature. Pour point is a measure of the temperature, in degrees Centigrade, at which the sample will begin to pour. Below that temperature the composition may generally be regarded as a solid. Thermogravimetric analysis (TGA) is a test which measures volatility by measuring the weight percent of sample remaining at various temperatures as the temperature is raised in a slow, uniform manner. When a sample's TGA indicates that at least 80% remains at 233° C., the sample is considered sufficiently nonvolatile to be useful in lube oil formulations.

Synthetic lubricant components which are expected to be used as lubricants should contain olefin oligomers having about twenty carbon atoms and greater. Thus, the only preferred separation step is to remove all olefin oligomers having less than about twenty carbon atoms. These lower carbon number oligomers may be removed before or after the hydrogenation step.

The process of this invention is further illustrated by the following examples.

EXAMPLES 1 and 2

Cyclohexane (415 g) and nickel-copper-chromium oxide (Ni-Cu-Cr) catalyst (15.0 g of powder passing #40 screen) were charged to a one gallon stirred autoclave. The clave was flushed with nitrogen and 22 g of $BF_3$ was charged. Temperature was maintained at 30–36° C. as a 4:1:1 weight ratio $C_4:C_{10}:C_{14}$ alpha olefin mixture (1250 g) was slowly added over a one hour and 50 minute period. Also present in the olefin mixture was 13.63 g of 1-butanol. The contents were stirred at autogenous pressure for two hours more. Pressure decreased from 85 to 78 psig (at $32\pm1°$ C.). Water (300 ml) was added. After one-half hour of stirring, the clave was vented. An 834.03 g aliquot of top layer was washed three times with 300 ml portions of water and stripped on a rotary evaporator to a maximum bath temperature of 93° C. at 35 mm Hg to remove monomer. The remaining liquid weighed 620 g. Liquid chromatography indicated a number average and weight average carbon number of 20.2 and 22.5, respectively, with about 55% of the molecules below $C_{20}$.

By comparison, when the reaction was repeated, but without Ni-Cu-Cr catalyst (Example 2), the number average and weight average carbon numbers were 17.6 and 18.3, respectively, with 85% of the molecules below $C_{20}$. Fluids for use as lubricants need to be greater than $C_{20}$.

When the material of this example was hydrogenated at 210° C. and 2,000 psig over the same Ni-Cu-Cr catalyst and fractionated so that 53% was removed overhead, the bottoms liquid, a clear and colorless fluid, had the following properties:
Number average: 25.21
Weight average: 27.16
Pour point, °F: $<-50$
Kinematic viscosity at 210° F., cs: 3.62
Viscosity index: 112
% remaining in TGA at 233° C.: 76

These properties indicate this fluid has excellent qualities for a crankcase lubricant.

EXAMPLE 3

Example 1 was essentially repeated except that 12 g of nickel oxide replaced the 15 g of Ni-Cu-Cr catalyst and only 20 g of $BF_3$ was used. The number average and weight average carbon numbers were 23.6 and 25.7, respectively, with 38% of the material below $C_{20}$. When hydrogenated and fractionated as in Example 1, so that 17% of the material was taken overhead, the bottoms product had the following properties:
Number average C no.: 34.1
Weight average C no.: 36.1
Pour point, °F.: $<-50$
Viscosity, 210° F.: 4.63
Viscosity index: 101
% left in TGA at 233° C: 89

EXAMPLE 4

Example 1 was essentially repeated except that prior to introduction of the $BF_3$, the clave was flushed with hydrogen, pressured to 100 psig with hydrogen, and heated to 200° C. over a 65 minute period. After cooling, the hydrogen was vented and 20 g of $BF_3$ (rather than 22 g in Example 1) was charged and the essential procedure of Example 1 was repeated. The oligomer obtained had a number average and weight average carbon number of 24.2 and 26.0, respectively, with 40% below $C_{20}$. Hydrogenation and fractionation as in Examples 1 and 3 resulted in a fluid with the following properties:
Number average C no.: 31.1
Weight average C no.: 33.3
Pour point, °F.: $-60$
Viscosity, 210° F.: 4.49
Viscosity index: 91
% left in TGA at 233° C.: 88

EXAMPLE 5

Example 3 was essentially repeated except that cobaltous carbonate ($CoCO_3$) replaced the NiO. The oligomer had a number average and weight average carbon number of 25.7 and 28.4, with 22% below $C_{20}$.

EXAMPLE 6

Example 3 was essentially repeated except 10 g of nickel fluoride ($NiF_2$) replaced the 12 g of NiO. The oligomer had a number average and weight average carbon number of 26.8 and 29.2, respectively, with 16% below $C_{20}$.

EXAMPLE 7

Example 6 was repeated except cobaltous fluoride ($CoF_2$) replaced the $NiF_2$. The product had a number average and weight average carbon number of 20.4 and 21.4, respectively, with 50% below $C_{20}$.

EXAMPLE 8

Example 1 was essentially repeated with the following exceptions. Only 20 g of $BF_3$ was used, only 5 g of NI-Cu-Cr catalyst was used, and the olefin mixture consisted of a 3:1:1 weight ratio of propylene/decene-1/tetradecene-1. The product oligomer had a number average and weight average carbon number of 22.5 and 25.2, respectively, with 40% below $C_{20}$. When hydrogenated and fractionated as in Examples 1 and 3, the product resulted in a fluid with the following properties:
Number average C no.: 28.1
Weight average C no.: 29.4
Pour point, °F.: −50
Viscosity, 210° F.: 3.71
Viscosity index: 90
% left in TGA at 233° C.: 68
These and other examples are summarized in Table I.

TABLE I
BF₃ OLIGOMERIZATION PROMOTED BY TRANSITION METAL COMPOUNDS

| Example | Wt. % BF₃ | Olefin* Mixture | Add'n Temp., °C. | Holding Temp., °C. | Added Component | Wt. Avg. No. | % Below C₂₀ | Kinematic Viscosity, 210° C., cs | VI | Point, °F. | % Left at 233° C. |
|---|---|---|---|---|---|---|---|---|---|---|---|
| 1 | 1.76 | A | 35 | 35 | Ni—Cu—Cr | 23 | 55 | 3.62 | 112 | <−50 | 76 |
| 2 | 1.76 | A | 35 | 35 | None | 18 | 85 | — | — | — | — |
| 3 | 1.60 | A | 33 | 33 | NiO | 26 | 38 | 4.63 | 101 | <−50 | 89 |
| 4 | 1.60 | A | 34 | 34 | Hydrogenated Ni—Cu—Cr | 26 | 40 | 4.49 | 91 | −60 | 88 |
| 5 | 1.60 | A | 33 | 33 | CoO | 28 | 22 | 4.91 | 77 | −35 | 82 |
| 6 | 1.60 | A | 33 | 33 | NiF₂ | 29 | 16 | 4.30 | 94 | −40 | 77 |
| 7 | 1.60 | A | 32 | 32 | CoF₂ | 21 | 50 | — | — | — | — |
| 8 | 1.60 | B | 33 | 33 | Ni—Cu—Cr | 25 | 40 | 3.71 | 90 | −50 | 68 |
| 9 | 1.60 | A | 32 | 32 | Co—Cu—Cr | 18 | 90 | — | — | — | — |
| 10 | 1.12 | A | 33 | 120 (2 hrs) | Hydrogenated | 29 | 15 | | | | |
| | | | 33 | 120 (4 hrs) | Ni—Cu—Cr | 30 | 14 | 4.34 | 95 | <−50 | 77 |
| 11 | 1.14 | C | 22 | 33 | Ni—Cu—Cr | 25 | 36 | 3.72 | 99 | <−50 | 73 |

Conditions:
Cyclohexane solvent, ~2 hour additional time and 2 hour holding time BF₃ in molar excess of 1-butanol
*A = 4:1:1 weight ratio C₄/C₁₀/C₁₄ alpha olefins
B = 3:1:1 weight ratio C₃/C₁₀/C₁₄ alpha olefins
C = 0.71:1 weight ratio C₃/C₁₀ alpha olefins It may be seen from Table I that Example 2, where no catalyst was used, shows a very high percentage of product which has less than twenty carbon atoms, the cutoff point for a useful synthetic lubricant fluid. Example 9, using a mixture of cobalt, copper and chromium oxide, also had this problem.

Many modifications may be made in the method of this invention without departing from its scope which is defined only by the appended claims. For example, it would be expected that one skilled in the art could change the BF₃ promoter, the temperature, the pressure or the modes of addition from those actually employed herein in trying to maximize the conversion or the oligomer properties.

We claim:
1. A process for oligomerizing mono olefins comprising contacting a mixture of alpha mono olefins having between 3 and 18 carbon atoms, inclusive, with a catalyst comprising boron trifluoride in the presence of an inorganic promoter containing a transition metal cation, under oligomerization conditions.

2. The process of claim 1 in which the mixture of alpha mono olefins consists essentially of low molecular weight alpha olefins having 3 to 5 carbon atoms and higher molecular weight alpha olefins having 8 to 18 carbon atoms.

3. The process of claim 1 in which the catalyst is present in an amount of from 0.2 to 3.0 weight percent.

4. The process of claim 1 in which the inorganic promoter contains a transition metal cation selected from the group consisting of nickel, copper, cobalt and chromium.

5. The process of claim 4 in which the inorganic promoter is selected from the group consisting of elemental nickel, elemental copper, nickel oxide, copper oxide, chromium oxide, nickel fluoride, cobaltous carbonate, cobaltous fluoride, and cobalt tetrafluoroborate, and mixtures thereof.

6. The process of claim 1 in which the inorganic promoter is present in an amount of from 0.005 to 3.0 weight percent.

7. The process of claim 1 in which a protonic promoter is employed in connection with the catalyst, the promoter being selected from the group consisting of alcohols carboxylic acids and water.

8. The process of claim 7 in which the protonic promoter is 1-butanol.

9. The process of claim 1 in which less than 30 weight percent of an inert organic solvent is employed.

10. The process of claim 1 in which the oligomerization reaction is conducted at a temperature in the range of about 25° to 125° C. and a pressure that is autogenous.

11. The process of claim 1 in which the oligomerized olefins are subsequently hydrogenated.

12. A process for oligomerizing mono olefins comprising contacting a mixture of alpha mono olefins which consists essentially of low molecular weight alpha olefins having 3 to 5 carbon atoms and higher molecular weight alpha olefins having 8 to 18 carbon atoms, with a catalyst comprising boron trifluoride in the presence of an inorganic promoter containing a transition metal cation selected from the group consisting of nickel, copper, cobalt and chromium.

13. The process of claim 12 in which the catalyst is present in an amount of from 0.2 to 3.0 weight percent.

14. The process of claim 12 in which the inorganic promoter is selected from the group consisting of elemental nickel, elemental copper, nickel oxide, copper oxide, chromium oxide, nickel fluoride, cobaltous carbonate, cobaltous fluoride and cobalt tetrafluoroborate, and mixtures thereof.

15. The process of claim 12 in which the inorganic promoter is present in an amount of from 0.005 to 3.0 weight percent.

16. The process of claim 12 in which a protonic promoter is employed in connection with the catalyst, the promoter being selected from the group consisting of alcohols, carboxylic acids and water.

17. The process of claim 16 in which the protonic promoter is 1-butanol.

18. The process of claim 12 in which less than 30 weight percent of an inert organic solvent is employed.

19. The process of claim 12 in which the oligomerization reaction is conducted at a temperature in the range of about 25° to 125° C. and a pressure that is autogenous.

20. The process of claim 12 in which the oligomerized olefins are subsequently hydrogenated.

21. A process for oligomerizing mono olefins comprising contacting
a. A mixture of alpha olefins which consists essentially of
   (1) at least one low molecular weight alpha olefin having 3 to 5 carbon atoms and
   (2) at least one higher molecular weight alpha olefin having 8 to 18 carbon atoms, with
b. 0.2 to 3.0 weight percent of a catalyst comprising boron trifluoride in the presence of
c. 0.005 to 3.0 weight percent of an inorganic promoter which contains a transition metal cation selected from the group consisting of nickel, copper, cobalt and chromium, at a temperature in the range of about 25° to 125° C. and a pressure that is autogenous.

22. The process of claim 21 in which the inorganic promoter is selected from the group consisting of elemental nickel, elemental copper, nickel oxide, copper oxide, chromium oxide, nickel fluoride, cobaltous carbonate, cobaltous fluoride and cobalt tetrafluoroborate, and mixtures thereof.

23. The process of claim 21 in which a protonic promoter is employed in connection with the catalyst, the promoter being selected from the group consisting of alcohols, carboxylic acids and water.

24. The process of claim 23 in which the protonic promoter is 1-butanol.

25. The process of claim 21 in which less than 30 weight percent of an inert organic solvent is employed.

26. The process of claim 21 in which the oligomerized olefins are subsequently hydrogenated.

27. A process for the production of a synthetic lubricant component comprising
a. oligomerizing a mixture of alpha mono olefins having between 3 and 18 carbon atoms, inclusive, by contacting the mixture with boron trifluoride in the presence of an inorganic promoter containing a transition metal cation, at a temperature sufficient to produce a crude oligomer product,
b. neutralizing the crude oligomer product,
c. removing the organic layer from the neutralized crude oligomer product,
d. hydrogenating the oligomers in the removed organic layer, and
e. stripping off the molecules having less than 20 carbon atoms, the balance being the synthetic lubricant component.

28. The process of claim 27 in which the mixture of alpha mono olefins consists essentially of
a. at least one low molecular weight alpha olefin having 3 to 5 carbon atoms, and
b. at least one higher molecular weight alpha olefin having 8 to 18 carbon atoms.

29. The process of claim 28 in which the weight ratio of the low molecular weight alpha olefins to the higher molecular weight alpha olefins ranges from about 0.5:1 to 3:1.

30. The process of claim 27 in which the catalyst is present in an amount of from 0.2 to 3.0 weight percent.

31. The process of claim 27 in which the inorganic promoter contains a transition metal cation selected from the group consisting of nickel, copper, cobalt and chromium.

32. The process of claim 27 in which the inorganic promoter is selected from the group consisting of elemental nickel, elemental copper, nickel oxide, copper oxide, chromium oxide, nickel fluoride, cobaltous carbonate, cobaltous fluoride and cobalt tetrafluoroborate, and mixtures thereof.

33. The process of claim 27 in which the inorganic promoter is present in an amount of from 0.005 to 3.0 weight percent.

34. The process of claim 27 in which a protonic promoter is employed in connection with the catalyst, the promoter being selected from the group consisting of alcohols, carboxylic acids and water.

35. The process of claim 34 in which the protonic promoter is 1-butanol.

36. The process of claim 27 in which less than 30 weight percent of an inert organic solvent is employed.

37. The process of claim 27 in which the oligomerization reaction is conducted at a temperature in the range of about 25° to 125° C. and a pressure that is autogenous.

38. A synthetic lubricant component having a viscosity at 210° F. of between 3.5 and 5.0 centistokes being produced by oligomerizing a mixture of alpha mono olefins which consists essentially of low molecular weight alpha olefins having 3 to 5 carbon atoms and higher molecular weight alpha olefins having 8 to 18 carbon atoms, by means of contacting the alpha olefins with boron trifluoride in the presence of an inorganic promoter containing a transition metal cation, under oligomerization conditions, and subsequently hydrogenating the oligomerized olefins.

39. The synthetic lubricant component of claim 38 in which the weight ratio of the low molecular weight alpha olefins to the higher molecular weight alpha olefins ranges from about 0.5:1 to 3:1.

40. The synthetic lubricant component of claim 38 in which the catalyst is present in an amount of from 0.2 to 3.0 weight percent.

41. The synthetic lubricant component of claim 38 in which the inorganic promoter contains a transition metal cation selected from the group consisting of nickel, copper, cobalt and chromium.

42. The synthetic lubricant component of claim 38 in which the inorganic promoter is selected from the group consisting of elemental nickel, elemental copper, nickel oxide, copper oxide, chromium oxide, nickel fluoride, cobaltous carbonate, cobaltous fluoride and cobalt tetrafluoroborate, and mixtures thereof.

43. The synthetic lubricant component of claim 38 in which the inorganic promoter is present in an amount of from 0.005 to 3.0 weight percent.

44. The synthetic lubricant component of claim 38 in which a protonic promoter is present during the oligomerization, the promoter being selected from the group consisting of alcohols, carboxylic acids and water.

45. The synthetic lubricant component of claim 44 in which the protonic promoter is 1-butanol.

46. The synthetic lubricant component of claim 38 in which less than 30 weight percent of an inert organic solvent is present during oligomerization.

47. The synthetic lubricant component of claim 38 in which the oligomerization reaction is conducted at a temperature in the range of about 25° to 125° C. and a pressure that is autogenous.

* * * * *